(12) United States Patent
Li et al.

(10) Patent No.: US 10,987,389 B2
(45) Date of Patent: Apr. 27, 2021

(54) ANTI-TUMOR TRADITIONAL CHINESE MEDICINE MICROBIAL FERMENTATION PREPARATION AND A PREPARATION METHOD AND APPLICATION THEREOF

(71) Applicants: Xingyao Li, Changtu (CN); Yeming Li, Huanggu Shenyang (CN)

(72) Inventors: Xingyao Li, Changtu (CN); Yeming Li, Huanggu Shenyang (CN)

( * ) Notice: Subject to any disclaimer, the term of this patent is extended or adjusted under 35 U.S.C. 154(b) by 0 days.

(21) Appl. No.: 15/308,831

(22) PCT Filed: Apr. 10, 2015

(86) PCT No.: PCT/CN2015/076286
§ 371 (c)(1),
(2) Date: Nov. 3, 2016

(87) PCT Pub. No.: WO2015/172618
PCT Pub. Date: Nov. 19, 2015

(65) Prior Publication Data
US 2017/0165307 A1    Jun. 15, 2017

(30) Foreign Application Priority Data
May 15, 2014    (CN) .......................... 201410207183.4

(51) Int. Cl.
| | | |
|---|---|---|
| *A61K 36/07* | (2006.01) | |
| *A61K 36/8945* | (2006.01) | |
| *A61K 36/8964* | (2006.01) | |
| *A61K 36/899* | (2006.01) | |
| *A61K 35/36* | (2015.01) | |
| *A61K 36/02* | (2006.01) | |
| *A61K 36/06* | (2006.01) | |
| *A61K 36/074* | (2006.01) | |
| *A61K 36/232* | (2006.01) | |
| *A61K 36/236* | (2006.01) | |
| *A61K 36/35* | (2006.01) | |
| *A61K 36/428* | (2006.01) | |
| *A61K 35/64* | (2015.01) | |
| *A61K 35/618* | (2015.01) | |
| *A61K 36/487* | (2006.01) | |
| *A61K 36/536* | (2006.01) | |
| *A61K 36/539* | (2006.01) | |
| *A61K 36/708* | (2006.01) | |
| *A61K 36/74* | (2006.01) | |
| *A61K 36/03* | (2006.01) | |
| *A61K 36/355* | (2006.01) | |
| *A61K 36/69* | (2006.01) | |
| *A61K 36/748* | (2006.01) | |
| *A61K 36/8994* | (2006.01) | |

(52) U.S. Cl.
CPC .............. *A61K 36/07* (2013.01); *A61K 35/36* (2013.01); *A61K 35/618* (2013.01); *A61K 35/64* (2013.01); *A61K 36/02* (2013.01); *A61K 36/03* (2013.01); *A61K 36/06* (2013.01); *A61K 36/074* (2013.01); *A61K 36/232* (2013.01); *A61K 36/236* (2013.01); *A61K 36/35* (2013.01); *A61K 36/355* (2013.01); *A61K 36/428* (2013.01); *A61K 36/487* (2013.01); *A61K 36/536* (2013.01); *A61K 36/539* (2013.01); *A61K 36/69* (2013.01); *A61K 36/708* (2013.01); *A61K 36/74* (2013.01); *A61K 36/748* (2013.01); *A61K 36/899* (2013.01); *A61K 36/8945* (2013.01); *A61K 36/8964* (2013.01); *A61K 36/8994* (2013.01); *A61K 2236/19* (2013.01)

(58) Field of Classification Search
CPC .... A61K 2300/00; A61K 36/02; A61K 36/03; A61K 36/06; A61K 36/07; A61K 36/074; A61K 36/232; A61K 36/236; A61K 36/35; A61K 36/355; A61K 36/428; A61K 36/487; A61K 36/536; A61K 36/539; A61K 36/69; A61K 36/708; A61K 36/74; A61K 36/748; A61K 36/8945; A61K 36/8964; A61K 36/899; A61K 36/8994; A61K 2236/19; A61K 35/36; A61K 35/618; A61K 35/64; A23V 2002/00; A23V 2250/211; A23V 2250/186; A23K 20/179; A23L 33/105; A23L 33/12; A23L 5/44; C12P 23/00; C12Q 1/44
See application file for complete search history.

(56) References Cited

U.S. PATENT DOCUMENTS

2014/0065131 A1* 3/2014 Kelly ...................... A23L 31/00
424/115

FOREIGN PATENT DOCUMENTS

CN            101773636        *   7/2010

OTHER PUBLICATIONS

Zhao et al."Anti-Tumor Activities of Andrographolide, a Diterpene from Andrographis Paniculata, by Inducing Apoptosis and Inhibiting VEGF Level", J. Asian Nat. Prod. Res.May 2008; 10(5):pp. 473-479.*

(Continued)

*Primary Examiner* — Deborah K Ware
(74) *Attorney, Agent, or Firm* — Chun-Ming Shih; Lanway IPR Services

(57) ABSTRACT

An anti-tumor traditional Chinese medicine, a preparation method therefor, and uses thereof. This traditional Chinese medicine is prepared by leavening of *Pleurotus* sp. and *Dioscorea bulbifera*, pangolin scales, rhubarb, oyster, stiff silkworm, kelp, selfheal, *Ligusticum wallichii*, barbat skullcap, honeysuckle flower, *Oldenlandia diffusa*, *Radix trichosanthis*, *Rhizoma anemarrhenae* *Scutellaria baicalensis*, *Angelica sinensis*, *Psoralea corylifolia*, Lucid ganoderma, and coix seed.

7 Claims, No Drawings

Specification includes a Sequence Listing.

(56) References Cited

OTHER PUBLICATIONS

Dr. Pack's Summary #252 Anti-Tumor Activity of Andrographis Paniculata. Rainbow Grocery Cooperative, Inv. 2016, See entire summary, one page.*

* cited by examiner though it has no toxic effect. Effects: relieving heat and toxin due to fire, cooling blood, stopping bleeding, removing stasis and dispersing accumulation. Clinical application: treating extravasated blood due to blood heat, constipation due to actual heat, etc.

ANTI-TUMOR TRADITIONAL CHINESE MEDICINE MICROBIAL FERMENTATION PREPARATION AND A PREPARATION METHOD AND APPLICATION THEREOF

TECHNICAL FIELD

The present invention relates to the field of traditional Chinese medicine preparations, and in particular to an anti-tumor traditional Chinese medicine microbial fermentation preparation and a preparation method and application thereof.

BACKGROUND OF THE PRESENT INVENTION

Human tumors are formed by the malignant transformation of normal cells under the action of carcinogenic factors. The cells are rapidly proliferated out of control, the infiltration and spread of poorly differentiated or highly differentiated cancer cells damage surrounding normal cells, and the cancer cells are metastasized nearby and distantly, until vital organs are exhausted to death.

Various kinds of cancer cells have been found around the world at present. There are millions of patients having malignant tumors around the world every year, and the number of patients is on the rise. Cancers pose a serious threat to the human health.

SUMMARY OF THE PRESENT INVENTION

The technical problem to be solved by the present invention is to provide a microbial fermentation parathion of an anti-tumor traditional Chinese medicine which has the effects of promoting blood circulation and removing blood stasis, resolving hard lump, calming endogenous wind and relieving pain, expelling pus, treating coagulation by purgation and inducing astringency, and a preparation method and application thereof. By using the traditional Chinese medicine and in combination with a modern preparation technique, tumor cells are inhibited and killed, so that the pains of the patients are relieved, and the life of the patients is prolonged.

An anti-tumor traditional Chinese medicine microbial fermentation preparation is provided, which is prepared by mixing raw traditional Chinese medicines and a fermentation extract, wherein the raw medicines include the following components in part by weight: 15 to 40 parts of *Dioscorea bulbifera*, 2 to 30 parts of pangolin scales, 5 to 35 parts of *Rheum officinale*, 2 to 30 parts of *Concha ostreae*, 5 to 40 parts of *Bombyx* batryticatus, 5 to 25 parts of kelp, 5 to 30 parts of *Prunella vulgaris*, 2 to 20 parts of *Ligusticum wallichii*, 2 to 30 parts of *Sculellaria barbata*, 2 to 30 parts of *Flos lonicerae*, 8 to 40 parts of *Oldenlandia diffusa*, 2 to 30 parts of *Radix trichosanthis*, 2 to 40 parts of *Rhizoma anemarrhenae*, 2 to 35 parts of *Radix scutellariae*, 2 to 35 parts of *Radix angelicae sinensis*, 8 to 30 parts of *Fructus psoraleae*, 2 to 30 parts of lucid ganoderma, and 2 to 30 parts of *Semen coicis;* there are 15 to 40 parts by weight of the fermentation extract; and the fermentation extract is *Pleurotus* sp., which has been preserved in China General Microbiological Culture Collection Center (CGMCC) on Apr. 14, 2014, and the preservation number is CGMCC No. 9060.

Further, the raw medicines include the following components in part by weight: 25 parts of *Dioscorea bulbifera*, 10 parts of pangolin scales, 15 parts of *Rheum officinale*, 10 parts of *Concha ostreae*, 15 parts of *Bombyx* batryticatus, 12 parts of kelp, 15 parts of *Prunella vulgaris*, 10 parts of *Ligusticum wallichii*, 15 parts of *Sculellaria barbata*, 15 parts of *Flos lonicerae*, 20 parts of *Oldenlandia diffusa*, 15 parts of *Radix trichosanthis*, 12 parts of *Rhizoma anemarrhenae*, 15 parts of *Radix scutellariae*, 15 parts of *Radix angelicae sinensis*, 20 parts of *Fructus psoraleae*, 15 parts of Lucid ganoderma, and 15 parts of *Semen coicis*; and there are 25 parts by weight of the fermentation extract.

A preparation method of the fermentation extract *Pleurotus* sp. is as follows: *Pleurotus* sp. is inoculated to a FDA solid culture medium and then cultured for 70 h to 120 h at 20° C. to 35° C. to obtain a purely cultured single colony of *Pleurotus* sp., i.e., a fermentation extract of *Pleurotus* sp.

The traditional Chinese medicine preparation is a capsule, a tablet, a pill, powder and/or oral liquid.

The traditional Chinese medicine preparation is powder.

A preparation method of the anti-tumor traditional Chinese medicine microbial fermentation preparation is provided, including the following steps of:

(1) weighing raw medicine components and grinding these components into fine powder;

(2) weighing a fermentation extract matched to the components in step (1); and (3) mixing the components in step (1) with the fermentation extract in step (2) to obtain the preparation.

An application of the anti-tumor traditional Chinese medicine microbial fermentation preparation is provided: the preparation is applied in medicines for treading tumor diseases.

The tumor diseases include lung cancer, gastric cancer, esophagus cancer, rectal cancer, brain cancer, liver cancer, renal cancer and the like.

The anti-tumor traditional Chinese medicine microbial fermentation preparation provided by the present invention is a modern Chinese medicine designed in accordance with a traditional Chinese medicine prescription principle of Monarch, Minister, Assistant and Guide. The effects of the used raw medicines are as follows.

*Dioscorea bulbifera* is neutral in nature and bitter in taste, and contains diosbulbin A-H, 8-epidiosbulbin E acetate, diosgenin, D-sorbitol, 2,4,6,7-tetrahydroxy-9,10-dihydrophenanthrene, 2,4,5,6-tetrahydroxyphenantyhrene, 4-hydroxy(2-trans-3',7'-dimethylocta-2',6'-dienyl)-6-methoxyacetophenone, 4,6-dihydroxy-2-O-(4'-hydroxybutylpacetophenone, dihydrodioscorine, and the like. The following is recorded in Bencao Jingshu: xanthate root has the function of relieving heat at Shaoyin, so that pharyngitis recovers because of no hyperactivity of ministerial fire. Poisoning by snake and dog bit is also because that the blood system is damaged by heat. The bitter-cold nature has the function of cooling the blood, and xanthate root is capable of resolving hundreds of toxins because it is grown in the soil.

Pangolin scales are scales of a Manidae animal pangolin, are efficient at channeling and dispersing, and have functions of promoting blood circulation and dredging collaterals, diminishing swelling and expelling pus, dispelling wind and relieving pain, and promoting lactation.

*Rheum officinale* has effects of relieving stagnancy, eliminating dampness and heat, purging intense heat, cooling blood, removing stasis, detoxifying and the like. The *Rheum officinale* is bitter in taste and cold in nature. Channel tropism: spleen, stomach, large intestine, liver, and pericardium channel. Effects: relieving stagnancy, eliminating dampness and heat, purging intense heat, cooling blood, removing stasis, and detoxifying. Indications: excess heat constipation, heat accumulation in chest, endoretention of damp heat, icterus, gonorrhea, edematous fullness of the abdomen, difficult urination, red eyes, sore throat, mouth sore, stomach heat vomiting, hematemesis, hemoptysis, rhinorrhagia, hematochezia, hematuria, blood accumulation, amenorrhea, postpartum stasis and stomachache, abdominal mass accumulation, bruises, heat toxin carbuncle, erysipelas, and empyrosis. In the *Rheum officinale*, main components causing diarrhea are anthraquinone glycoside and dianthrone glucoside, whose purgative effects are higher than corresponding aglucones. The anthraquinone glycoside includes: chrysophanol-1-monoglucoside or chrysophanein, emodin-6-monoglucoside, aloe-emodin-8-monoglucoside, physcion monoglucoside, and rhein-8-monoglucoside. *Rheum palmatum* L. further contains emodin diglucoside, aloe-emodin diglucoside, and chrysophanol diglucoside.

The dianthrone glucoside includes sennosides A, B, C, D, E and F. The purgative effect of the *Rheum officinale* is proportional to the content of the associative rhein, and free anthraquinones have no purgative effect. The sennosides have a higher purgative effect than the anthraquinone glycoside, but their content is far less than the later. The free anthraquinones mainly include: chrysophanol, emodin, physcion, aloe-emodin and rhein. The *Rheum officinale* further contains rheotannic acid and related substances thereof, such as gallic acid, catechin and tetrarin.

The *Concha ostreae* is shells of Ostreidae animals, such as *Ostrea rivularis, Crassostrea gigas, Crassostrea talienwhanensis* and *Ostrea denselamellosa*. Nature, taste and channel tropism: salty; slightly cold; liver, gallbladder, and kidney. Effects: tranquilizing the liver, calming endogenous wind, and nourishing yin; and calming the nerves, restraining yang and tonifying yin, resolving hard lump, and inducing astringency. The *Concha ostreae* is used for treating horrified insomnia, dizziness and tinnitus, crewels and phlegm node, spontaneous sweating and night sweating, spermatorrhea and leucorrhea, stomachache and acid regurgitation. The calcined oyster shell has an effect of inducing astringency, and is used for treating spontaneous sweating and night sweating, spermatorrhea and leucorrhea, and stomachache and acid regurgitation.

The *Bombyx* batryticatus is dried bodies of larvae of 4- to 5-instar silkworms as bombycidae insect that are infected by *Beauveria bassiana*. It has a slightly fishy smell and is slightly salty in taste, and it is mainly used in epilepsy, swollen sore throat, submaxillary lymph nodes, facioplegia, skin itch and other diseases. The *Bombyx* batryticatus is a common traditional Chinese medicine having effects of dispelling the wind, spasmolysis, reducing phlegm and resolving masses, and is clinically used for treating corporeal masses, such as nodes, sore throat, crewels, wind sores, urticaria and the like due to its channeling function. The *Bombyx* batryticatus is mainly used for dispelling the wind, relieving convulsion, reducing phlegm and resolving masses, and is used in epilepsy, swollen sore throat, submaxillary lymph nodes, facioplegia and skin itch. The *Bombyx* batryticatus mainly contains protein and fat, and also contains various amino acids and microelements, such as iron, zinc, copper, manganese and chromium. The white powder on the surface of white muscardin silkworm contains ammonium oxalate. The alcohol/water leachate of the *Bombyx* batryticatus has hypnotic and anti-convulsion effects on mice and domestic rabbits, and its extract has a high anticoagulation effect both in vivo and in vitro. The *Bombyx* batryticatus powder has an excellent hypoglycemic effect. The in-vitro tests indicate that the *Bombyx* batryticatus powder has a slightly bacteriostatic effect on *Staphylococcus aureus* and *Pseudomonas aeruginosa*, and its alcohol extract can inhibit the breath of human hepatoma carcinoma cells in vitro and thus can be used for treating the rectal tumor type polyposis. The *Bombyx* batryticatus treats the headache due to pathogenic wind-heat, hot eyes, pharyngalgia, *rubella* and *pruritus*. The *Bombyx* batryticatus is acrid and divergent, and its channel tropism is liver and lung. The *Bombyx* batryticatus has functions of dispelling the external wind, eliminating the wind-heat, relieving pain and relieving itching. The *Bombyx* batryticatus is used for treating the headache due to the wind-heat of liver channel, hot eyes, the lacrimation induced by irritation of the wind and the like, and is commonly compatible with wind-dispelling and heat-clearing medicines, such as *Folium mori, Herba equiseti hiemalis* and *Herba schizonepetae*, for example, white batryticated silkworm powder (*Standards of Diagnosis and Treatment*). The *Bombyx* batryticatus is used for treating the wind-heat attack, swollen sore throat and hoarseness, and can be compatible with *Radix platycodonis, Mentha haplocalyx, Herba schizonepetae, Radix saposhnikoviae, Radix liquiritiae* and the like, for example, Liuwei decoction (Yanhou Miji). The *Bombyx* batryticatus treats *rubella* and *pruritus*. For example, in Taiping Shenghui Fang, the *Bombyx* batryticatus is powdery and taken orally for treating urticaria. The *Bombyx* batryticatus can be grinded into powder alone, or compatible with wind-dispelling and itch-relieving medicines, such as *Periostracum cicada* and *Mentha haplocalyx*. The *Bombyx* batryticatus treats the subcutaneous nodule and crewels. As the *Bombyx* batryticatus is salty in taste and can soften heard lump and reduce phlegm, so it can be used for treating subcutaneous nodule and crewels. The *Bombyx* batryticatus can be used alone in powder, or be compatible with phlegm-reducing and mass-resolving medicines, such as *Bulbus fritillariae thunbergii, Prunella vulgaris* and *Fructus forsythia*. The *Bombyx* batryticatus can also be used for treating mastitis, mumps, furunculosis, carbuncle and the like, and can be compatible with heat-clearing and detoxifying medicines, such as *Lonicera japonica, Fructus forsythia, Radix isatidis* and *Radix scutellariae*. The *Bombyx batryticatus* treats epilepsy and is salty, acrid and mild, and its channel tropism is liver and lung. As the *Bombyx* batryticatus can calm endogenous wind, relieve convulsion and reduce phlegm, so it is suitable for patients with infantile convulsion, epilepsy and phlegm-heat. When the *Bombyx* batryticatus is used for treating high-fever tiqueurs, it can be compatible with *Periostracum cicada, Ramulus uncariae* cum uncis and *Flos chrysanthemi*. When the *Bombyx* batryticatus is used for treating patients with acute infantile convulsion and phlegm asthma, it is compatible with scorpio, *Rhizoma gastrodiae, cinnabaris, Calculus bovis*, bile arisaema and the like, for example, Qianjin San (Shoushi Baoyuan). If the *Bombyx* batryticatus is used for treating children chronic diarrhea caused by spleen deficiency and chronic convulsion, it should be compatible with medicines for replenishing qi, tonifying spleen and clamping endogenous wind and convulsion, such as *Codonopsis pilosula, Rhizoma atractylodis macrocephalae, Rhizoma gastrodiae* and scorpio, for example, Xingpi San (Gujin Yitong). If the *Bombyx* batryticatus is used for treating tetanus and opisthotonos, it is compatible with scorpio, centipede, *Ramulus uncariae* cum uncis and the like, for example, Zuofeng San (*Standards of Diagnosis and Treatment*). The *Bombyx* batryticatus is also used for treating meridians attacked by wind, and facial paralysis.

The kelp is salty in taste, cold in nature and non-toxic. Its channel tropism is liver, stomach and kidney. Effects: dissolving phlegm and softening hard mass; and, promoting urination and diminishing swelling. Indications: crewels; goiter and tumor; dysphagia; and, hernia edema. The kelp is used for treating goiter and tumor, crewels, spermary gall, and phlegm edema. Its chemical components include algin, mannito, galactan, laminine, laminarin, glutamic acid, aspartic acid, proline, vitamin B1, vitamin C, vitamin P, iodine, potassium and the like. The major functions of the kelp is softening hard mass, dissolving phlegm and promoting urination. The kelp is used for treating goiter and tumor, crewels, spermary gall, and phlegm edema.

The *Prunella vulgaris* is cold in nature, and sweet, acrid and slightly bitter in taste, and has effects of clearing liver fire, removing stasis and swelling, clearing away heat and removing toxin, expelling phlegm to arrest coughing, and coolinf blood for hemostasis. The *Prunella vulgaris* is suitable for scrofula, goiter, breast carbuncle, dizziness, facial paralysis, arthralgia and myalgia, phthisis, metrorrhagiam, morbid leucorrhea, acute infectious jaundice type hepatitis, bacillary dysentery and the like. Modern pharmacological researches show that the *Prunella vulgaris* has an effect of reducing blood pressure and can dilate blood vessels, and the rutin contained in the the *Prunella vulgaris* has an anti-inflammatory action and can reduce the vascular permeability, fragility and liver lipid. The *Prunella vulgaris* also has an effect of resisting cancer cells.

The *Ligusticum wallichii* is acrid in taste and warm in nature. Its channel tropism is liver, gallbladder and heart. The *Ligusticum wallichii* has effects of invigorating the blood circulation, promoting the circulation of qi, dispelling the wind and relieving pain. Chuanxiongzine can dilate coronary artery, increase the blood flow of the coronary artery, improve the blood oxygen supply of myocardium, and reduce the oxygen consumption of myocardium. Chuanxiongzine also can dilate cerebral vessels, reduce the vascular resistance, significantly increase the blood flow of the brain and limbs, and improve microcirculation; and can reduce the surface activity of blood platelets, inhibit the aggregation of blood platelets, and prevent the formation of thrombus. Neutral components of the ferulic acid contained in the *Ligusticum wallichii* play a promoting role in a small dosage, while play an inhibition role for uterine smooth muscle in a large dosage. The decoctum of the *Ligusticum wallichii* has a sedative effect on the central nervous system of animals, and plays a significant and lasting role in reducing blood pressure. The *Ligusticum wallichii* can quicken the absorption of the local hematoma of the fracture, promote the porosis, suppress various kinds of bacillus, and have an effect of resisting the deficiency of vitamin E and an antihistamine and cholagogue effect. The *Ligusticum wallichii* contains chuanxiongzine, perlolyrine, ligustilide, wallichilide, 3-butylideniphthalide, 3-butylidene-7-hydroxyphthalide, butylphthalide, (3S)-3-butyl-4-hydroxyphthalide, 3-n-bntyl-3,6,7-trihydroxy-4,5,6,7-tetrahydrophthalide, neocindilide, senkyunolide, senkyunolide B, C, D, E, F, G, H, I, J, K, L, M, N, O and P, (E)-senkyunolide, 2-methoxy-4-(3-mnethoxy-1-propenyl)pheneol, 2-(1-oxopentyl)-benzoic acid methyl ester, 5-hydroxymethyl-6-endo-3-methoxy-4-hydroxyphenyl-8-oxa-bicyclo(3.2.1)-oct-3-one, 4-hydroxy-3-methoxy styrene, 1-hydroxy-1-(3-methoxy-4-hydroxyphenyl)ethane, vanillic acid, coffeic acid, protocatechuic acid, ferulic acid, chrysophanic acid, sedanonic acid, L-isoleucyl-L-valine anhydride, L-valyl-L-valinc achydride, perlolyrine, chuanxiongol, uracil, trimethylamine-HCL, chloine chloride, palmitic acid, vanillin, 1-acetyl-β-carboline, spathulenol, β-sitosterol, linoleic acid, dilinoyl palmitoyl glyceride, sucrose and the like.

The *Sculellaria barbata* is acrid and bitter in taste and cold in nature. Its channel tropism is lung, liver and kidney. The *Sculellaria barbata* treats hematemesis, rhinorrhagia, bloody stranguria, dysentery, jaundice, throat pain, pulmonary abscess, crewels, sore toxin, cancer, bruises and cuts and snake bites. The *Sculellaria barbata* has functions of clearing away heat and removing toxin, activating blood circulation and removing stasis, relieving swelling and pain, resisting against tumors and the like. The whole *Sculellaria barbata* contains carthamidin, iso-carthamidin, scutellarein, scutellarin, β-sitosterol, steraric acid, alkaloid polysaccharides and the like. Wogonin, scutervulin, rivularin, naringenin, apigenin, hispedulin, eriodictyol, suteolin, 5,7,4-trihydroxy-6-methoxyflavanone, 4-hydroxywogonin, 7-hydroxy-5,8-dimethoxyflavane, p-hydroxybenzaldehyde, p-hydroxybenzylacetone, p-coumaric acid, protocatechuic acid, ursolic acid, phytosterol, phytosteryl-β-D-glucoside and the like may be separated from the overground part of the *Sculellaria barbata*.

The *Flos lonicerae*, also called honeysuckle, is sweet in taste. Its channel tropism is lung, heart and stomach. The *Flos lonicerae* has effects of clearing away heat and removing toxin, resisting inflammation, and tonifying deficiency, and is mainly used for treating tumescence diseases, fever due to warm diseases, carbuncle due to heat toxin, tumors and the like. The *Flos lonicerae* has a certain effect on dizziness, thirst, hidrosis, enteritis, bacillary dysentery, measles, pneumonia, epidemic encephalitis B, epidemic cerebrospinal meningitis, acute mastitis, septicemia, appendicitis, skin infection, ulcer and furunculosis, erysipelas, parotitis, suppurative tonsillitis and the like. The *Flos lonicerae* has been praised as a good medicine for clearing away heat and removing toxin. It is sweet and cold in nature and fragrant in smell. Its cold nature clears away heat but does not hurt the stomach, and its fragrance may eliminate pathogens. The *Flos lonicerae* may scatter wind heat and remove blood toxin, and has a significant effect on various heat diseases, such as general fever, exanthesis, spots, carbuncle due to heat toxin, sore throat and the like. Modern researches show that, the *Flos lonicerae* contains chlorogenic acid, luteolin and other pharmacologically active components, which have a high inhibition effect on various kinds of pathogenic bacteria and upper respiratory infection pathpgenic virus, such as hemolytic streptococcus and *Staphylococcus aureus*. In addition, the *Flos lonicerae* can boost immunity, resist early pregnancy, protect liver, resist against tumors, diminish inflammation, clear away heat, stop bleeding (coagulate blood), prevent the intestinal tract from absorbing cholesterol, and the like, so it has very board clinic applications. The *Flos lonicerae* can be compatible with other medicines for treating more than 40 diseases, such as respiratory tract infection, bacillary dysentery, acute urinary tract infection and hypertension.

The *Oldenlandia diffusa* is bitter and light in taste, and cold in nature. Its main effects are as follows: clearing away heat, removing toxin, promoting urination and dehumidifying. Its indications are as follows: dyspnea with cough caused by lung heat; sore throat; intestinal carbuncle; furuncle and sores; venomous snake bites; edema; dysentery; enteritis; jaundice due to damp-heat; and various kinds of cancers. The whole *Oldenlandia diffusa* contains asperuloside, asperulosidic acid, deacetylasperulosidicacid, geniposidic acid, scandoside, scandodide methyl ester, 6-O-p-hydroxycinnamoyl scandoside methylester, 6-O-p-methoxycinnamlyl scandoside methyl ester, 2-methyl-3- hydroxyanthraquinone, 2-methyl-3-methoxyanthraquinon, 2-methyl-3-hydroxy-4-methoxyanthraquinone, ursolic acid, β-sitosterol, hentriacon-tane, stigmasterol, oleanolic acid, β-sitosterol-β-D-glucoside, p-coumaric acid and the like.

The *Radix trichosanthis* is roots of the cucurbitaceous plant *Trichosanthes kirilowii*, and is a traditional Chinese medicine for clearing heat and purging fire. Its specific effects are as follows: clearing heat and purging fire; promoting the secretion of saliva or body fluid and quenching thirst; and, expelling pus and diminishing swelling. The *Radix trichosanthis* is sweet and slightly bitter in taste, and slightly cold in nature, and its channel tropism is lung and stomach. Effects: clearing heat, promoting the secretion of saliva or body fluid, diminishing swelling and expelling pus. Indications: polydipsia caused by fever diseases, dry cough with lung heat, consumptive thirst caused by internal heat, ulcer and pyogenic infections. The *Radix trichosanthis* treats the fever thirst, consumptive thirst, jaundice, hemoptysis caused by lung dryness, carbuncle and haemorrhoid. Trichosanthin is separated from the fresh root juice, and various kinds of amino acids are obtained: o-hydroxymethylserine, aspartic acid, citrulline, serine, glutamic acid, threonine, valine, tyrosine, phenylalanine, histidine, lysine, arginine, ornithine and peptides, ribose, xylose, arabinose, galactose and the like. The roots contain polysaccharides for rising the blood sugar, such as *Trichosanthes* polysaccharides A, B, C, D and E; and the roots and stems contain polysaccharides having antitumor activity and immunoactivity, which consist of glucose, galactose, fructose, mannose, xylose and a large amount of protein. The fresh roots further contain 7-stigmaster-3β-ol, bryonolic acid, cucurbitacin B and D, and 23,24-dihydrocucurbitacin B.

The *Rhizoma anemarrhenae* is bitter and sweet in taste and cold in nature. Its channel tropism is lung, stomach and kidney. The *Rhizoma anemarrhenae* has effects of clearing heat and purging intense fire, promoting the secretion of saliva or body fluid and moistening dryness, and is used for treating fever diseases caused by exogenous pathogenic factors, polydipsia caused by hyperpyrexia, cough caused by lung heat, hectic fever, consumptive thirst caused by the internal heat, and constipation caused by intestine dryness. The *Rhizoma anemarrhenae* is a medicine for clearing heat and purging fire, and is mainly used for treating the warm heat disease, polydipsia caused by hyperpyrexia, cough type asthma, cough caused by dryness, constipation, hectic fever, insomnia with dysphoria, and stranguria with turbid urine. The roots contain total saponins, including timosaponin A-I, A-II, A-III, A-IV, B-I and B-II, where the timosaponin A-I is sarsasaponin β-D-galactopyranoside, and the timosaponin A-III is a disaccharide formed by sarsasaponin and anemarrhena disaccharide, and the timosaponin A-III. The saponins in the *Rhizoma anemarrhenae* include sarsasaponin, markogenin, and gitogenin. The saponin chinonin previously separated from the *Rhizoma anemarrhenae* is a mixture of markogenin, timosaponin A-III, timosaponin A-IV, timosaponin B and the like. Iso-sarsasapogenin or other saponins are also separated. The *Rhizoma anemarrhenae* also contains flavonoids, such as mangiferin and isomangiferin; alkaloids, such as choline and nicotinamide; organic acids, such as tannic acid and nicotinic acid; and four kinds of *Rhizoma anemarrhenae* polysaccharides. In addition, the *Rhizoma anemarrhenae* also contains many kinds of metal elements, such as iron, zinc, manganese, copper, chromium and nickel; phlegmatic temperament, reducing sugars and the like. The *Rhizoma anemarrhenae* is clinically applied to polydipsia caused by fever diseases, cough with lung heat, dry cough caused by Yin deficiency, hectic fever, consumptive thirst caused by Yin deficiency, and constipation caused by intestine dryness.

The *Radix scutellariae* is bitter in taste and cold in nature. Its channel tropism is lung, gallbladder, spleen, stomach, large intestine and small intestine. *Encyclopedia of Traditional Chinese Medicines*: "dogwood and fossil fragment serve as the Guide. Side effects will be caused if *Radix scutellariae* is used with welsh-onion. The function of *Radix scutellariae* will be replaced by cinnabar, peony and *Veratrum nigrum* if they are used together. When *Radix scutellariae* is used with *Radix bupleuri*, it can regulate the exterior and interior and harmonizing Shaoyang; when used with large-headed atractylodes rhizome, it can clear heat and prevent abortion; when used with *Pinellia ternate*, it can diffuse acrid and descend bitter; when used with *Coptis chinensis*, it can clear heat and expel dampness; and when used with immature bitter orange and *Mangnolia officinalis*, it can promote digestion and harmonize the stomach. The *Radix scutellariae* can clear away heat and eliminate dampness, purge intense heat and remove toxin, stop bleeding, and prevent miscarriage. The *Radix scutellariae* is mainly used for treating the warm-heat disease, upper respiratory infection, cough with lung heat, jaundice due to damp-heat, pneumonia, dysentery, hemoptysis, hot eyes, threatened abortion, hypertension, carbuncle and furuncle, and the like.

The *Radix angelicae sinensis* is sweet, acrid and bitter in taste, and mild in nature. Its channel tropism is liver, heart and spleen. Effects: enriching the blood, promoting blood circulation, regulating menstruation and relieving pain, and moistening dryness and lubricating the intestines. Indications: diseases caused by the blood deficiency; irregular menstruation; amenorrhea; dysmenorrheal; abdominal mass; metrorrhagia and metrostaxis; stomachache caused by deficiency-cold; paralysis; numbness; intestine dryness and debata; dysentery; ulcers and sores; and, traumatic injuries. The *Radix angelicae sinensis* contains volatile oils and non-volatile components; neutral oil components in the volatile oils, including butylidene phthalide, β-pinene, α-pinene, camphene, p-cymene, β-phellandrene, myrcene, allo-ocimene, 6-n-butyl-cycloheptadiene-1, 4,2-methyl-dodecan-5-one, acetophenone, 6-bisabolene, isoacroraene, acoradiene, cuparene, α-cedrene, ligustilide, n-butyl tetrahydrolactone, n-butyl lactone, n-butene lactone, N-dodecanol, bergapten and the like; and, other components, such as stigmasterol, sitosterol, stigmasterol-D-glucoside, tetradecanol-1, scopletin and the like.

The *Fructus psoraleae* has the functions of invigorating the kidney, strengthening Yang, securing essence, reducing urination, relieving lumbago caused by the kidney deficiency, reducing frequent urination, reducing infantile enuresis, relieving kidney leakage, warming spleen and stopping diarrhea, absorbing qi and relieving asthma. The *Fructus psoraleae* is mainly used for treating the asynodia caused by the kidney deficiency, the soreness, weakness and cold pain of the waist and knees, the seminal emission due to the kidney deficiency, enuresis, frequent urination and the like. The *Fructus psoraleae* is also used for treating the diarrhea caused by the Yang deficiency of spleen and kidney, and the deficiency-cold and dyspnea with cough due to failure of kidney to promote respiration.

The channel tropism of the *Lucid ganoderma* is the heart, liver, spleen, lung and kidney. The *lucid ganoderma* are mainly used for treating the consumptive disease, cough, asthma, insomnia, dyspepsia, malignant tumors and the like. An animal pharmacology manifestation test shows that the *lucid ganoderma* plays an inhibition role in the nervous system, plays a role of lowering blood pressure and strengthening the contractive force of the heart in the circulatory system, plays a role of eliminating phlegm in the respiratory system, and also have the effects of protecting liver, enhancing the immune function, resisting bacteria and the like. The chemical components of the lucid ganoderma mainly include ergosterol, fungal lysozyme and acid proteinase, L-mannitol and enol. Its water-soluble extract contains water-soluble proteins; various amino acids, such as asparaginic acid, glutamic acid, arginine, lysine, leucine, alanine, tryptophan, threonine, proline, methionine, phenylalanine, serine and the like; and, polypeptides and polysaccharides. The extract also contains resin, lactone, coumarin and the like.

The *Semen coicis* is sweet and mild in taste and slightly cold in nature, has the functions of invigorating the spleen, eliminating dampness, clearing away heat and eliminating pus, and is used for treating spleen deficiency, diarrhea, edema, beriberi, leucorrhea, damp, arthralgia, intestinal carbuncle, lung paralysis and other diseases.

All the raw materials and equipments required by the present invention are goods purchased in the market.

The present invention has the following beneficial effects:

1. The preparation provided by the present invention has the effect of skilling tumor cells and the functions of supporting the healthy energy and comprehensively regulating the body. Moreover, as the used raw medicines are traditional Chinese medicines and their dosages are within the scope of pharmacopeia and the national standard scope, these raw medicines are safe and reliable, without any toxic and side effect.

2. The present invention uses a zymocyte biotechnology, without any toxic and side effect and any dependency. All active constituents are decomposed into small molecules, and present in form of amino acids, linolenic acids, polypeptides and the like. Small-molecular active proteins having cell activity have significant effects on the repairing and improvement of the eight systems of the human body.

3. The active constituents contain fat-soluble constituents, have rapid effects, and are absorbed by blood in cells by the mucosa. The active constituents can activate repair factors in the blood of the self-immune repair cell nucleuses and promote the body to restore the original physiological functions. The active constituents can lock the blood of biological cells, and really provide the human body with polypeptides active substances of cell-nucleus blood cells with positive energy.

DETAILED DESCRIPTION OF THE PRESENT INVENTION

In order to further describe the present invention, the present invention will be specifically described by the following embodiments.

An anti-tumor traditional Chinese medicine microbial fermentation preparation is provided, which is prepared by mixing raw traditional Chinese medicines and a fermentation extract, wherein the raw medicines include the following components in part by weight: 15 to 40 parts of *Dioscorea bulbifera*, 2 to 30 parts of pangolin scales, 5 to 35 parts of *Rheum officinale*, 2 to 30 parts of *Concha ostreae*, 5 to 40 parts of *Bombyx* batryticatus, 5 to 25 parts of kelp, 5 to 30 parts of *Prunella vulgaris*, 2 to 20 parts of *Ligusticum wallichii*, 2 to 30 parts of *Sculellaria barbata*, 2 to 30 parts of *Flos lonicerae*, 8 to 40 parts of *Oldenlandia diffusa*, 2 to 30 parts of *Radix trichosanthis*, 2 to 40 parts of *Rhizoma anemarrhenae*, 2 to 35 parts of *Radix scutellariae*, 2 to 35 parts of *Radix angelicae sinensis*, 8 to 30 parts of *Fructus psoraleae*, 2 to 30 parts of *lucid ganoderma*, and 2 to 30 parts of *Semen coicis*;

there are 15 to 40 parts by weight of the fermentation extract; and the fermentation extract is *Pleurotus* sp., which has been preserved in China General Microbiological Culture Collection Center (CGMCC) on Apr. 14, 2014, and the preservation number is CGMCC No. 9060.

A preparation method of the fermentation extract *Pleurotus* sp. is as follows: *Pleurotus* sp. is inoculated to a FDA solid culture medium and then cultured for 70 h to 120 h at 20° C. to 35° C. to obtain a purely cultured single colony of *Pleurotus* sp., i.e., a fermentation extract of *Pleurotus* sp.

The traditional Chinese medicine preparation is capsules, tablets, pills, powder and/or oral liquid.

A preparation method of the powdery traditional Chinese medicine preparation is provided, including the following steps of:

(1) weighing raw medicine components and grinding these components into fine powder;

(2) weighing a fermentation extract matched to the components in step (1); and (3) mixing the components in step (1) with the fermentation extract in step (2) to obtain the preparation.

An application in medicines for treading tumor diseases is provided.

The tumor diseases include lung cancer, gastric cancer, esophagus cancer, rectal cancer and the like.

Embodiment 1

In the traditional Chinese medicine compound powder prepared by the above method, raw medicines by weight are as follows: 15 kg of *Dioscorea bulbifera*, 2 kg of pangolin scales, 5 kg of *Rheum officinale*, 2 kg of *Concha ostreae*, 5 kg of *Bombyx* batryticatus, 5 kg of kelp, 5 kg of *Prunella vulgaris*, 2 kg of *Ligusticum wallichii*, 2 kg of *Sculellaria barbata*, 2 kg of *floc lonicerae*, 8 kg of *Oldenlandia diffusa*, 2 kg of *Radix trichosanthis*, 2 kg of *Rhizoma anemarrhenae*, 2 kg of *Radix scutellariae*, 2 kg of *Radix angelicae sinensis*, 8 kg of *Fructus psoraleae*, 2 kg of *Lucid ganoderma*, and 2 kg of *Semen coicis*; and there is 15 kg by weight of the fermentation extract.

A preparation method of the fermentation extract *Pleurotus* sp. is as follows: *Pleurotus ostreatus* (i.e., *Pleurotus* sp.) is inoculated to a FDA solid culture medium and then cultured for 70 h at 20° C. to obtain a purely cultured single colony of *Pleurotus* sp., i.e., a fermentation extract of *Pleurotus* sp.

Embodiment 2

In the traditional Chinese medicine compound powder prepared by the above method, raw medicines by weight are as follows: 25 kg of *Dioscorea bulbifera*, 10 kg of pangolin scales, 15 kg of *Rheum officinale,* 10 kg of *Concha ostreae,* 15 kg of *Bombyx* batryticatus, 12 kg of kelp, 15 kg of *Prunella vulgaris,* 10 kg of *Ligusticum wallichii,* 15 kg of *Scutellaria barbata,* 15 kg of *Flos lonicerae,* 20 kg of *Oldenlandia diffusa,* 15 kg of *Radix trichosanthis,* 12 kg of *Rhizoma anemarrhenae,* 15 kg of *Radix scutellariae,* 15 kg of *Radix angelicae sinensis,* 20 kg of *Fructus psoraleae,* 15 kg of *Lucid ganoderma,* and 15 kg of *Semen coicis*; and there is 25 kg by weight of the fermentation extract.

A preparation method of the fermentation extract *Pleurotus* sp. is as follows: *Pleurotus ostreatus* (i.e., *Pleurotus* sp.) is inoculated to a FDA solid culture medium and then cultured for 96 h at 28° C. to obtain a purely cultured single colony of *Pleurotus* a fermentation extract of *Pleurotus* sp.

Embodiment 3

In the traditional Chinese medicine compound powder prepared by the above method, raw medicines by weight are as follows: 40 kg of *Dioscorea bulbifera,* 30 kg of pangolin scales, 35 kg of *Rheum officinale,* 30 kg of *Concha ostreae,* 40 kg of *Bombyx* batryticatus, 25 kg of kelp, 30 kg of *Prunella vulgaris,* 20 kg of *Ligusticum wallichii,* 30 kg of *Scutellaria barbata,* 30 kg of *Flos lonicerae,* 40 kg of *Oldenlandia diffusa,* 30 kg of *Radix trichosanthis,* 40 kg of *Rhizoma anemarrhenae,* 35 kg of *Radix scutellariae,* 35 kg of *Radix angelicae sinensis,* 30 kg of *Fructus psoraleae,* 30 kg of *Lucid ganoderma,* and 30 kg of *Semen coicis*; and there is 40 kg by weight of the fermentation extract.

A preparation method of the fermentation extract *Pleurotus* sp. is as follows: *Pleurotus ostreatus* (i.e., *Pleurotus* sp.) is inoculated to a FDA solid culture medium and then cultured for 120 h at 35° C. to obtain a purely cultured single colony of *Pleurotus* sp., i.e., a fermentation extract of *Pleurotus* sp.

Experiment

A suspension of 10% was prepared from the traditional Chinese medicine compound powder provided by the present invention and then stored in a refrigerator. The suspension would be shaken up before use.

Tumor strain: Heps, S180 and ESC were all commercially available products.

Animal: Kunming mice provided by the animal laboratories of Shenyang Pharmaceutical University and China Pharmaceutical University.

Method: referring to the following literatures:

Literature 1: chief editor Xu Shuyun. Methodology of Pharmacological Experiment, Beijing: People's Medical Publishing House 1982, 1115-1125.

Literature 2: China Academic Conference on Tumor Pharmacology and Chemotherapy: In-vivo Efficacy Test Procedures of Anticancer Drugs, internal data. 1989.

1. Effects of the Traditional Chinese Medicine Compound Powder on Heps Solid Tumor The results in Table 1 indicated that the traditional Chinese medicine compound powder provided by the present invention had a significant anticancer activity to the mouse transplantable Heps solid tumor when the oral administration dosage was 0.4 ml/10 g, 0.2 ml/10 g and 0.1 ml/10 g. The maximum inhibition rate at a high dosage was 59.54%, the minimum inhibition rate at a low dosage was 33.09%, and the P value was less than 0.05 after statistical treatment.

TABLE 1

Effects of the oral administration of the traditional Chinese medicine compound powder provided by the present invention on mouse Heps solid tumor

| Group | Dosage (ml/10 g × &) | Number of cases Beginning/End | Weight (g) Beginning/End | Tumor weight (g) (X ± SD) | Inhibition rate | P |
|---|---|---|---|---|---|---|
| NS | 0.2 × 8 | 20/20 | 21.76/24.63 | 3.27 ± 0.97 | | |
| 0.15% 5-Fu | 0.1 × 8 | 10/10 | 21.30/24.80 | 1.12 ± 0.85 | 65.75% | <0.01 |
| 10% | 0.4 × 8 | 10/8 | 21.50/21.00 | 1.32 ± 0.53 | 59.54% | <0.01 |
| compound | 0.2 × 8 | 10/10 | 22.55/22.50 | 1.59 ± 0.31 | 51.45% | <0.01 |
| powder | 0.1 × 8 | 10/10 | 21.65/23.25 | 1.69 ± 0.65 | 48.40% | <0.01 |
| NS | 0.2 × 8 | 20/20 | 18.20/22.40 | 1.36 ± 0.39 | | |
| 0.15% 5-Fu | 0.1 × 8 | 10/9 | 18.95/20.22 | 0.59 ± 0.27 | 56.62% | <0.01 |
| 10% | 0.4 × 8 | 9/9 | 19.22/21.67 | 0.76 ± 0.24 | 44.12% | <0.05 |
| compound | 0.2 × 8 | 9/8 | 19.00/21.56 | 0.81 ± 0.16 | 40.44% | <0.05 |
| powder | 0.1 × 8 | 9/9 | 18.67/21.39 | 0.91 ± 0.03 | 33.09% | <0.05 |
| NS | 0.2 × 9 | 12/12 | 21.63/24.50 | 2.53 ± 0.38 | | |
| 0.15% 5-Fu | 0.1 × 9 | 9/8 | 21.00/25.86 | 1.05 ± 0.54 | 58.55% | <0.01 |
| 10% | 0.4 × 9 | 9/9 | 20.72/24.00 | 1.13 ± 0.52 | 55.27% | <0.01 |
| compound | 0.2 × 9 | 9/9 | 20.78/26.00 | 1.41 ± 0.44 | 44.27% | <0.01 |
| powder | 0.1 × 9 | 9/9 | 21.00/22.78 | 1.48 ± 0.83 | 41.50% | <0.01 |

2. Effects of the Traditional Chinese Medicine Compound Powder on S180 Solid Tumor The results in Table 2 indicated that the traditional Chinese medicine compound powder provided by the present invention had a significant anticancer activity to the mouse transplantable S180 solid tumor when the oral administration dosage was 0.4 ml/10 g, 0.2 ml/10 g and 0.1 ml/10 g. The maximum inhibition rate at a high dosage was 62.36%, the minimum inhibition rate at a low dosage was 30.46%, and the P value was less than 0.05 after statistical treatment.

TABLE 2

Effects of the oral administration of the compound powder on mouse S180 solid tumor

| Group | Dosage (ml/10 g × &) | Number of cases Beginning/End | Weight (g) Beginning/End | Tumor weight (g) (X ± SD) | Inhibition rate | P |
|---|---|---|---|---|---|---|
| NS | 0.2 × 9 | 13/13 | 21.40/24.04 | 3.25 ± 0.70 | | |
| 0.15% 5-Fu | 0.2 × 9 | 9/9 | 20.78/20.00 | 1.87 ± 1.03 | 42.62% | <0.01 |
| 10% | 0.4 × 9 | 9/7 | 21.28/21.00 | 1.39 ± 0.53 | 57.41% | <0.01 |
| compound | 0.2 × 9 | 9/9 | 21.38/22.11 | 2.05 ± 0.91 | 36.92% | <0.05 |
| powder | 0.1 × 9 | 9/8 | 21.11/21.14 | 2.26 ± 0.81 | 30.46% | <0.05 |
| NS | 0.2 × 9 | 20/18 | 21.15/24.39 | 3.56 ± 0.54 | | |
| 0.15% 5-Fu | 0.2 × 9 | 10/10 | 21.80/24.70 | 1.36 ± 0.44 | 61.80% | <0.01 |
| 10% | 0.4 × 9 | 10/9 | 21.20/25.40 | 1.34 ± 0.33 | 62.36% | <0.01 |
| compound | 0.2 × 9 | 10/8 | 21.70/23.35 | 1.91 ± 0.33 | 46.63% | <0.01 |
| powder | 0.1 × 9 | 10/9 | 21.5/23.56 | 2.06 ± 0.41 | 42.14% | <0.01 |
| NS | 0.2 × 9 | 20/18 | 21.20/25.13 | 3.37 ± 0.43 | | |
| 0.15% 5-Fu | 0.2 × 9 | 10/10 | 21.30/23.60 | 1.33 ± 0.31 | 60.53% | <0.01 |
| 10% | 0.4 × 9 | 10/10 | 21.30/24.50 | 1.46 ± 0.53 | 56.68% | <0.01 |
| compound | 0.2 × 9 | 10/8 | 21.50/25.38 | 1.72 ± 0.46 | 43.96% | <0.01 |
| powder | 0.1 × 9 | 10/9 | 21.70/26.56 | 2.03 ± 0.58 | 39.76% | <0.01 |

3. Effects of the Traditional Chinese Medicine Compound Powder on ESC Solid Tumor The results in Table 3 indicated that the traditional Chinese medicine compound powder provided by the present invention had a significant anticancer activity to the mouse transplantable ESC solid tumor when the oral administration dosage was 0.4 ml/10 g, 0.2 ml/10 g and 0.1 ml/10 g. The maximum inhibition rate at a high dosage was 62.84%, the minimum inhibition rate at a low dosage was 41.98%, and the P value was less than 0.01 after statistical treatment.

TABLE 3

Effects of the oral administration of the compound powder on mouse Ehrlich Ascites Cancer (EAC) solid tumor

| Group | Dosage (ml/10 g × &) | Number of cases Beginning/End | Weight (g) Beginning/End | Tumor weight (g) (X ± SD) | Inhibition rate | P |
|---|---|---|---|---|---|---|
| NS | 0.2 × 9 | 19/19 | 22.58/25.79 | 3.83 ± 0.72 | | |
| 0.15% 5-Fu | 0.2 × 9 | 10/10 | 20.85/26.90 | 1.33 ± 0.63 | 65.36% | <0.01 |
| 10% | 0.4 × 9 | 10/9 | 20.80/29.69 | 1.51 ± 0.26 | 60.21% | <0.01 |
| compound | 0.2 × 9 | 10/10 | 21.20/28.00 | 1.82 ± 0.65 | 52.43% | <0.01 |
| powder | 0.1 × 9 | 10/10 | 20.20/29.80 | 2.22 ± 0.47 | 41.98% | <0.01 |
| NS | 0.2 × 9 | 20/19 | 20.60/25.89 | 3.69 ± 0.62 | | |
| 0.15% 5-Fu | 0.2 × 9 | 10/10 | 20.90/26.80 | 1.23 ± 0.43 | 64.85% | <0.01 |
| 10% | 0.4 × 9 | 10/8 | 20.80/28.50 | 1.41 ± 0.64 | 61.58% | <0.01 |
| compound | 0.2 × 9 | 10/9 | 21.00/30.44 | 1.53 ± 0.85 | 58.31% | <0.01 |
| powder | 0.1 × 9 | 10/9 | 20.80/31.43 | 1.59 ± 0.56 | 56.68% | <0.01 |
| NS | 0.2 × 9 | 20/20 | 20.03/23.55 | 3.96 ± 0.53 | | |
| 0.15% 5-Fu | 0.2 × 9 | 10/10 | 21.45/22.20 | 1.31 ± 0.65 | 66.85% | <0.01 |
| 10% | 0.4 × 9 | 10/9 | 21.05/20.61 | 1.87 ± 0.77 | 62.84% | <0.01 |
| compound | 0.2 × 9 | 10/9 | 21.65/22.98 | 1.63 ± 0.36 | 58.82% | <0.01 |
| powder | 0.1 × 9 | 10/9 | 20.85/22.56 | 2.04 ± 0.46 | 48.39% | <0.01 |

4. Acute Toxicity Test 20 mice with half males and half females were prepared. The mice took orally the traditional Chinese medicine compound powder provided by the present invention at a ratio of 5 g/kg (water) and continuously observed for 7 days, and no one had died. It was indicated that the LD50 of the traditional Chinese medicine compound powder provided by the present invention is above 5 g/kg.

In addition, the effects of the traditional Chinese medicine compound powder provided by the present invention on the EAC ascites had been preliminarily observed. The results indicated that the traditional Chinese medicine compound powder provided by the present invention were ineffective to the ascites.

In conclusion, the results of this research indicated that the traditional Chinese medicine compound powder provided by the present invention had the significant anticancer activity to the three tumor strains after the compound powder was continuously orally administrated for 9 days at a ratio of 4 g/kg, 2 g·kg and 1 g/kg. The inhibition rate could reach or exceed the standard (30) regulated in China, so it was indicated that the traditional Chinese medicine compound powder provided by the present invention had a significant antitumor effect. The acute toxicity test proved that the LD50 of the oral administration of the traditional Chinese medicine compound powder provided by the present invention was greater than 5 g/kg, and the toxicity was small. The current clinical observation also indicates that the traditional Chinese medicine compound powder provided by the present invention had a good curative effect on various malignant tumors. Therefore, it is worth performing deep clinical and preparation researches on the traditional Chinese medicine compound powder provided by the present invention.

5. Clinical Test

All patients had the diagnostic reports, the reports of X-ray photographs and CT photographs, pathological section reports and microscopic examination reports in hospitals around China, and 500 cases were observed. After half-year's observation, the cancers and symptoms such as lung cancer, intestinal cancer, gastric cancer and esophagus cancer had been improved to different extents. After the patients took the traditional Chinese medicine compound powder, their appetites and weights were increased, and they felt much better. Through the comparative observation before and after medication, the compound powder provided by the present invention has an anticancer function and has effects of controlling the tumor and improving body immunity.

The compound powder had treated 249 cases of lung cancer, the symptoms were improved, and the tumor was stably lessened to different extents through before-and-after comparison. Such clinical effects were significant. After the patients took the compound powder, they felt much better, their appetites and weights were increased, their pains were relieved, and their cough and dyspnea also got better. Moreover, majority of the patients who were completely bedridden could take part in outdoor activities, and some of the patients could work normally. The therapeutic effects were as shown in Table 4.

Detection of DNA of *Pleurotus* sp.

I. DNA Extraction

The fungi DNA was extracted by a FastDNA SPIN soil DNA extraction kit (MP Biomedicals, Santa Ana, Calif.).

II. PCR Amplification

PCR Amplification Primers:

```
ITS1:
5' CTTG GTCA TTTA GAGG AAGTAA3'

ITS4:
5' TCCT CCGC TTAT TGAT ATGC3'
```

PCR Amplification Procedure:

| | | |
|---|---|---|
| 94° C. | 2 min | |
| 94° C. | 30 s | |
| 55° C. | 45 s | 35 cycles |
| 72° C. | 1 min | |
| 72° C. | 7 min | |
| 10° C. | forever | |

III. Sequencing

The FOR product was sequenced by Shanghai Biotechnology Co., Ltd.

The result of the gene sequence was as follows:

```
CTCTCCGGGGGGAACCTTGGGGAGGGTCCTTTAATGATTCCCTTAG

GGAGTGGTGGTGGCCTTTAGGGGCCAGGTCCCGGTTCCATAGTTTTTC

ACCCCCCGTGGACTTTTGAAAGGTTTGGGGAATTGTTTTTCCAATTGTT

CAGATTGGTTTGCTGGGATTTAAACGTCTCGGTGTGACTACGCAGTCTA

TTTACTTACCCCCCCCCAAAGGAAGTTTTCGAAAGTCCATTAAAGGGCC
```

TABLE 4

Treatment analysis of the compound powder

| | Total number of patients: 500 | Effective (the number of patients) | Proportion (%) | Effectual (the number of patients) | Proportion (%) | Heal (the number of patients) | Proportion (%) | Ineffective (the number of patients) | Proportion (%) |
|---|---|---|---|---|---|---|---|---|---|
| Lung cancer | 249 | 221 | 88.7 | 60 | 24.1 | 6 | 2.4 | 28 | 11.3 |
| Gastric cancer | 78 | 71 | 91.1 | 24 | 30.8 | 1 | 1.3 | 7 | 8.9 |
| Esophagus cancer | 66 | 59 | 89.3 | 18 | 27.2 | 1 | 1.5 | 7 | 10.7 |
| Rectal cancer | 68 | 63 | 92.6 | 21 | 30.9 | 2 | 2.9 | 5 | 7.4 |

The total tumor inhibition rate was 82.8%, and the total effective rate was 96.5%.

Note: 39 patients were not visited due to unclear recorded addresses, so these patients were not recorded.

The results indicated that: through the clinical observation of the trail, the compound powder had a significant inhibition effect on patients having intermediate-stage or advanced-stage cancers, and could resist against the centers and lessen the tumors. Cancer cells were killed or dissolved, and then vanished from water or blood. The compound powder could prolong life, and is free of toxic and side effects, convenient to use, safe and reliable.

-continued
```
CTGGGCCTTTTAACCCTTAATCCAACTTTCACCAAGGATTTTTTGGCTT

TTGCCATGAAGGAAGAAGCAAGGAAAATGGGTAAAGAAAGGGAAATGCC

GAAATCCAGGGATCCTTGGATTCTTGGACCCCCCCTGCCCCCCCTGGTA

TTTCGGGGGGCCAGCCCGGTTGGGGGGCCATTAATTTTTCAAATCCCTT

TGGTTTTTTTCCAATTGTGATGTTTGGATTGTTGGGGGCTGCTGGCCTT

GACAGGTCGGCTCCTCTTAAATGCATTAGCAGGACTTCTCATTGCCTCT

GCGCATGATGTGATAATTATCACTCATCAATAGCACGCATGAATAGAGT
```

-continued
CCAGCTCTCTAATCGTCCGCAAGGACAATTTGACAATTGACCTCAAATC

AGGTAGACAGCCGGATTCT

IV. Comparison Results
Through Comparison With the Database of NCBI (National Center of Biotechnology Information as of the filing date of the present patent application, the results were as follows:

*Pleurotus ostreatus* isolate NW42618S ribosomal RNA gene (login ID: EU622251.1)

*Pleurotus ostreatus*, i.e., *Pleurotus* sp.

What is claimed is:

1. An anti-tumor Chinese medicine microbial fermentation preparation, comprising a mixture of raw Chinese medicines and a fermentation extract, wherein the raw medicines comprise the following components in part by weight: 15 to 40 parts of *Dioscorea bulbifera*, 2 to 30 parts of pangolin scales, 5 to 35 parts of *Rheum officinale*, 2 to 30 parts of *Concha ostreae*, 5 to 40 parts of *Bombyx batryticatus*, 5 to 25 parts of kelp, 5 to 30 parts of *Prunella vulgaris*, 2 to 20 parts of *Ligusticum wallichii*, 2 to 30 parts of *Sculellaria barbata*, 2 to 30 parts of *Flos lonicerae*, 8 to 40 parts of *Oldenlandia diffusa*, 2 to 30 parts of *Radix trichosanthis*, 2 to 40 parts of *Rhizoma anemarrhenae*, 2 to 35 parts of *Radix scutellariae*, 2 to 35 parts of *Radix angelicae sinensis*, 8 to 30 parts of *Fructus psoraleae*, 2 to 30 parts of *Lucid ganoderma*, and 2 to 30 parts of *Semen coicis*;

wherein there are 15 to 40 parts by weight of the fermentation extract; and the fermentation extract is *Pleurotus* sp.

2. The anti-tumor Chinese medicine microbial fermentation preparation of claim 1, wherein the raw medicines comprise the following components in part by weight: 25 parts of *Dioscorea bulbifera*, 10 parts of pangolin scales, 15 parts of *Rheum officinale*, 10 parts of *Concha ostreae*, 15 parts of *Bombyx batryticatus*, 12 parts of kelp, 15 parts of *Prunella vulgaris*, 10 parts of *Ligusticum wallichii*, 15 parts of *Sculellaria barbata*, 15 parts of *Flos lonicerae*, 20 parts of *Oldenlandia diffusa*, 15 parts of *Radix trichosanthis*, 12 parts of *Rhizoma anemarrhenae*, 15 parts of *Radix scutellariae*, 15 parts of *Radix angelicae sinensis*, 20 parts of *Fructus psoraleae*, 15 parts of *Lucid ganoderma*, and 15 parts of *Semen coicis*; and there are 25 parts by weight of the fermentation extract.

3. The anti-tumor Chinese medicine microbial fermentation preparation of claim 1, wherein a preparation method of the fermentation extract *Pleurotus* sp. is as follows: *Pleurotus* sp. is inoculated to a PDA solid culture medium and then cultured for 70 h to 120 h at 20° C. to 35° C. to obtain a purely cultured single colony of *Pleurotus* sp. for extraction to obtain the fermentation extract of *Pleurotus* sp.

4. The anti-tumor Chinese medicine microbial fermentation preparation of claim 1, wherein the fermentation extract *Pleurotus* sp, comprises the extract preserved in China General Microbiological Culture Collection Center (CGMCC) on Apr. 14, 2014, having preservation number CGMCC No. 9060.

5. The anti-tumor Chinese medicine microbial fermentation preparation of claim 1, wherein the Chinese medicine preparation is one of a capsule, a tablet, a pill, powder and/or oral liquid.

6. The anti-tumor Chinese medicine microbial fermentation preparation of claim 1, wherein the Chinese medicine preparation is powder.

7. A preparation method of the anti-tumor Chinese medicine microbial fermentation preparation of claim 6, comprising:

(1) weighing the raw medicine components and grinding these components into fine powder;

(2) weighing the fermentation extract matched to the components in step (1); and (3) mixing the components in step (1) with the fermentation extract in step (2) to obtain the preparation.

* * * * *

SEQUENCE LISTING

```
<160> NUMBER OF SEQ ID NOS: 3

<210> SEQ ID NO 1
<211> LENGTH: 653
<212> TYPE: DNA
<213> ORGANISM: pleurotus ostreatus
<220> FEATURE:
<221> NAME/KEY: gene
<222> LOCATION: (1)..(653)
<223> OTHER INFORMATION: Pleurotus Ostreatus

<400> SEQUENCE: 1
ctctccgggg ggaaccttgg ggagggtcct ttaatgattc ccttagggag tggtggtggc      60 ctttagggc caggtcccgg ttccatagtt ttttcacccc ccgtggactt ttgaaaggtt     120
tggggaattg tttttccaat tgttcagatt ggtttgctgg gatttaaacg tctcggtgtg    180
actacgcagt ctatttactt accccccccc aaaggaagtt ttcgaaagtc cattaaaggg    240
ccctgggcct tttaaccctt aatccaactt tcaccaagga tttttggct tttgccatga     300 aggaagaagc aaggaaaatg ggtaaagaaa gggaaatgcc gaaatccagg gatccttgga    360
ttcttggacc cccctgccc ccctggtat ttcgggggc cagcccggtt ggggggccat       420 taattttca aatcccttg gtttttttcc aattgtgatg tttggattgt tggggctgc       480 tggccttgac aggtcggctc ctcttaaatg cattagcagg acttctcatt gcctctgcgc    540
atgatgtgat aattatcact catcaatagc acgcatgaat agagtccagc tctctaatcg    600
tccgcaagga caatttgaca attgacctca aatcaggtag acagccggat tct           653

<210> SEQ ID NO 2
<211> LENGTH: 22
<212> TYPE: DNA
<213> ORGANISM: artificial sequence
<220> FEATURE:
<221> NAME/KEY: gene
<222> LOCATION: (1)..(22)
<223> OTHER INFORMATION: primer of the PCR for amplifying the Pleurotus
      Ostreatus sequences

<400> SEQUENCE: 2
cttggtcatt tagaggaagt aa                                              22

<210> SEQ ID NO 3
<211> LENGTH: 20
<212> TYPE: DNA
<213> ORGANISM: artificial sequence
<220> FEATURE:
<221> NAME/KEY: gene
<222> LOCATION: (1)..(20)
<223> OTHER INFORMATION: primer of the PCR for amplifying the Pleurotus
      Ostreatus sequences

<400> SEQUENCE: 3
tcctccgctt attgatatgc                                                 20
```